United States Patent
Segawa

(10) Patent No.: US 9,380,931 B2
(45) Date of Patent: Jul. 5, 2016

(54) ENDOSCOPE APPARATUS WHICH CAN DETECT TEMPERATURE OF DISTAL END PORTION

(71) Applicant: OLYMPUS CORPORATION, Tokyo (JP)

(72) Inventor: Kazunori Segawa, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/661,345

(22) Filed: Mar. 18, 2015

(65) Prior Publication Data
US 2015/0190042 A1 Jul. 9, 2015

Related U.S. Application Data

(63) Continuation of application No. PCT/JP2014/052081, filed on Jan. 30, 2014.

(30) Foreign Application Priority Data

Mar. 19, 2013 (JP) .................................. 2013-056906

(51) Int. Cl.
  *A61B 1/00* (2006.01)
  *A61B 1/12* (2006.01)
  (Continued)

(52) U.S. Cl.
  CPC .............. *A61B 1/127* (2013.01); *A61B 1/00006* (2013.01); *A61B 1/05* (2013.01); *A61B 1/128* (2013.01); *G02B 23/2476* (2013.01)

(58) Field of Classification Search
  CPC .... A61B 1/00006; A61B 1/127; A61B 1/128; G02B 23/2476; G02B 23/2492; G02B 7/008; H05B 1/025
  See application file for complete search history.

(56) References Cited

U.S. PATENT DOCUMENTS

| 2003/0168059 A1 | 9/2003 | Pacey |
| 2007/0073108 A1* | 3/2007 | Takahashi .............. A61B 1/051 600/169 |

(Continued)

FOREIGN PATENT DOCUMENTS

| EP | 1 803 388 A2 | 7/2007 |
| JP | 63-276198 A | 11/1988 |

(Continued)

OTHER PUBLICATIONS

International Search Report dated Mar. 4, 2014 issued in PCT/JP2014/052081.

(Continued)

*Primary Examiner* — John P Leubecker
(74) *Attorney, Agent, or Firm* — Scully, Scott, Murphy & Presser, P.C.

(57) ABSTRACT

An endoscope apparatus includes an objective optical system that is provided at a distal end portion of an insertion portion of an endoscope which can be inserted into a body cavity of a subject; a temperature sensor unit that detects a temperature of the distal end portion; a heating unit that can generate heat for preventing fogging of the objective optical system; a timer that measures a time period during which the temperature of the distal end portion detected by the temperature sensor unit is equal to or lower than a predetermined temperature; and a control unit that performs control so as to cause the heating unit to generate the heat when the time period measured by the timer continues for a predetermined time period or longer.

2 Claims, 2 Drawing Sheets

(51) Int. Cl.
*G02B 23/24* (2006.01)
*A61B 1/05* (2006.01)

(56) References Cited

U.S. PATENT DOCUMENTS

| | | | |
|---|---|---|---|
| 2012/0167882 A1* | 7/2012 | Wood | A61B 1/00082 |
| | | | 128/204.17 |
| 2013/0116507 A1* | 5/2013 | Segawa | A61B 1/00006 |
| | | | 600/109 |
| 2015/0313454 A1* | 11/2015 | Ide | A61B 1/0008 |
| | | | 600/129 |

FOREIGN PATENT DOCUMENTS

| | | |
|---|---|---|
| JP | 64-088128 A | 4/1989 |
| JP | 02-257926 A | 10/1990 |
| JP | 2006-000282 A | 1/2006 |
| JP | 2010-008314 A | 1/2010 |
| JP | 2013-034720 A | 2/2013 |

OTHER PUBLICATIONS

Japanese Office Action dated Sep. 24, 2014 issued in JP 2014-534300.

Partial Supplementary European Search Report dated Mar. 17, 2016 from related European Application No. 14 76 7667.0.

* cited by examiner

ENDOSCOPE APPARATUS WHICH CAN DETECT TEMPERATURE OF DISTAL END PORTION

CROSS REFERENCE TO RELATED APPLICATION

This application is a continuation application of PCT/JP2014/052081 filed on Jan. 30, 2014 and claims benefit of Japanese Application No. 2013-056906 filed in Japan on Mar. 19, 2013, the entire contents of which are incorporated herein by this reference.

BACKGROUND OF THE INVENTION

1. Field of the Invention

The present invention relates to an endoscope apparatus, and particularly to an endoscope apparatus which can detect a temperature of a distal end portion of an insertion portion of an endoscope.

2. Description of the Related Art

In a medical field, conventionally, observation within a body cavity of a living body has been performed using an endoscope apparatus. As the above-described endoscope apparatus, for example, there has been conventionally known an endoscope apparatus which has an elongated insertion portion that can be inserted into a body cavity of a living body, and which is configured to form an image of an object within the body cavity using an objective optical system disposed at a distal end portion of the insertion portion, pick up the formed image of the object to output the image as an image pickup signal, and display the image of the object according to the outputted image pickup signal at a display unit.

Further, in the above-described endoscope apparatus, for example, one having a defogging function as disclosed in Japanese Patent Application Laid-Open Publication No. 2006-000282 has been conventionally known. More specifically, Japanese Patent Application Laid-Open Publication No. 2006-000282 discloses a configuration in which a sensor for detecting a temperature of a distal end portion of an endoscope insertion portion is provided and a heater is made to operate according to an output signal from the sensor, thereby fogging of an observation optical system is prevented.

SUMMARY OF THE INVENTION

An endoscope apparatus according to one aspect of the present invention includes an objective optical system that is provided at a distal end portion of an insertion portion of an endoscope which can be inserted into a body cavity of a subject; a temperature sensor unit that detects a temperature of the distal end portion; a heating unit that can generate heat for preventing fogging of the objective optical system; a timer that measures a time period during which the temperature of the distal end portion detected by the temperature sensor unit is equal to or lower than a predetermined temperature; and a control unit that performs control so as to cause the heating unit to generate the heat when the time period measured by the timer continues for a predetermined time period or longer.

An endoscope apparatus according to one aspect of the present invention includes an objective optical system that is provided at a distal end portion of an insertion portion of an endoscope which can be inserted into a body cavity of a subject; a temperature sensor unit that detects a temperature of the distal end portion; a heating unit that can generate heat for preventing fogging of the objective optical system; an electric surgical apparatus that applies electrical energy to a portion to be treated located within the body cavity; and a control unit that performs control so as to cause the heating unit to generate the heat when detecting that the temperature detected by the temperature sensor unit is equal to or lower than a predetermined temperature and that the electric surgical apparatus is not running.

DETAILED DESCRIPTION OF THE PREFERRED EMBODIMENTS

An embodiment of the present invention will be described below with reference to the drawings.

Figure 1:
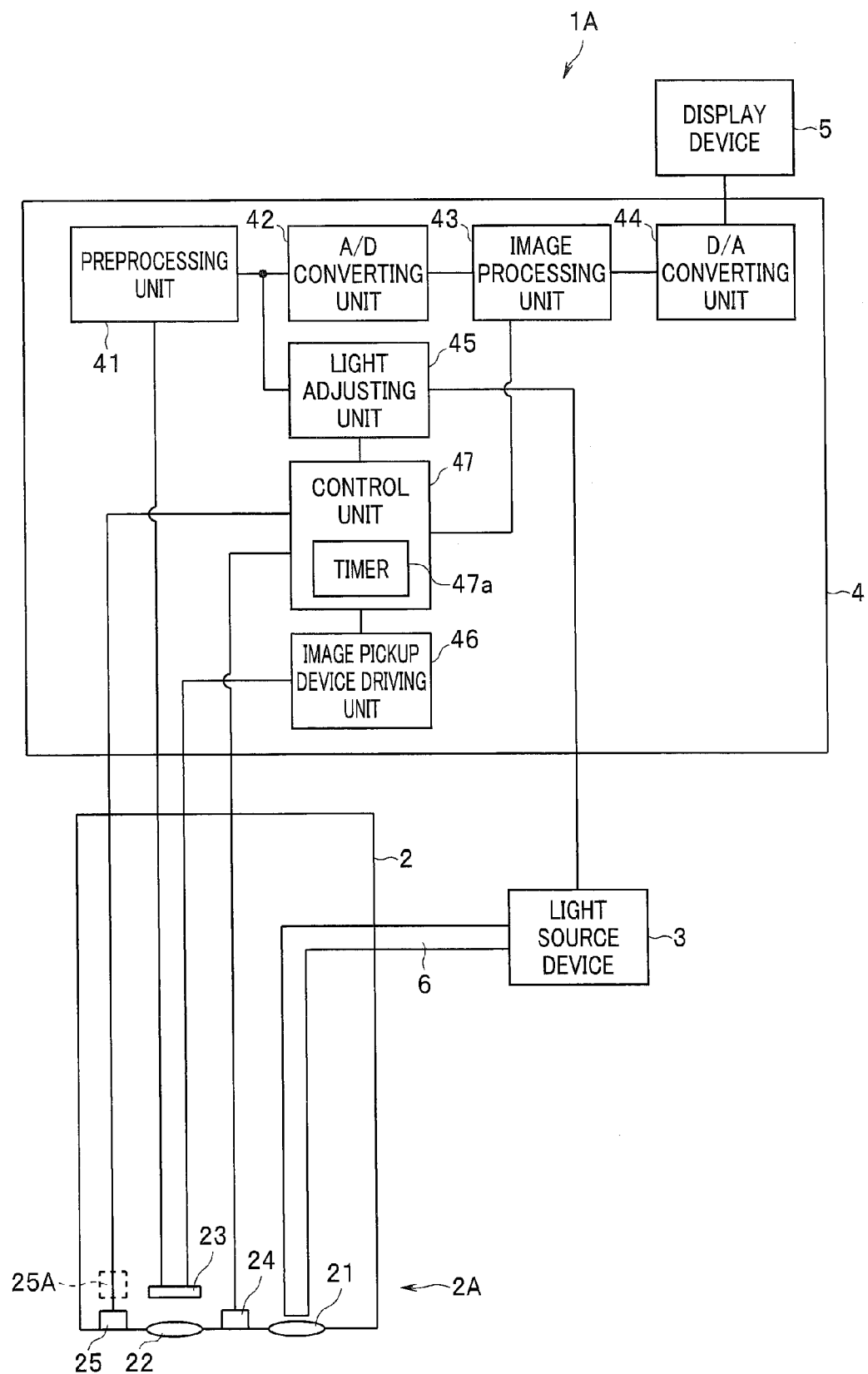
FIG. 1 is a diagram illustrating a configuration of main components of an endoscope apparatus according to an embodiment of the present invention.
Figure 2:
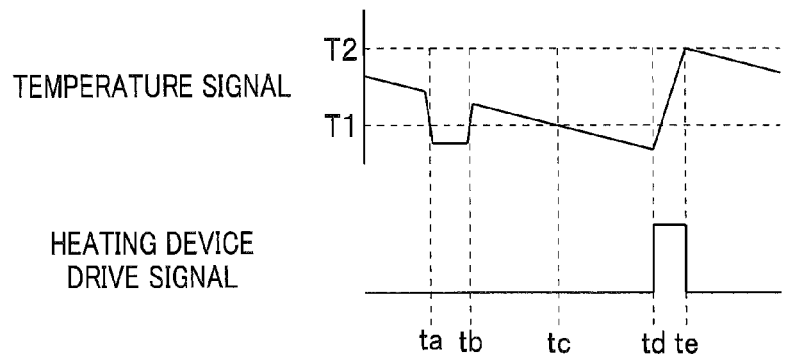
FIG. 2 is a diagram for explaining an example of control performed in the endoscope apparatus according to the embodiment of the present invention.

FIG. 1 and FIG. 2 relate to the embodiment of the present invention. FIG. 1 is a diagram illustrating a configuration of main components of an endoscope apparatus according to the embodiment of the present invention.

As illustrated in, for example, FIG. 1, an endoscope apparatus 1A includes an insertion portion which can be inserted into a body cavity of a subject and has an endoscope 2 which is configured to acquire an image of an object such as body tissue located within the body cavity, a light source device 3 which is configured to supply to the endoscope 2 an illumination light for illuminating the object, a processor 4 which is configured to generate and output a video signal according to the image acquired by the endoscope 2, and a display device 5 which is configured to display an image according to the video signal outputted from the processor 4. Further, a light guide 6 which is configured to transmit the illumination light supplied from the light source device 3 to a distal end portion 2A of the insertion portion is inserted into the insertion portion of the endoscope 2.

The endoscope 2 is configured so that an illumination optical system 21 that emits the illumination light transmitted through the light guide 6 toward the object, an objective optical system 22 that forms an image of a return light from the object illuminated with the illumination light, an image pickup device 23 whose image pickup face is disposed at an image formation position of the objective optical system 22, a heating device 24 that is disposed in the vicinity of the objective optical system 22, and a temperature sensor unit 25 that detects a temperature of the distal end portion 2A are provided at the distal end portion 2A.

The image pickup device 23 is configured to acquire an image of the object by being driven based on an image pickup device drive signal outputted from the processor 4, and generate an image pickup signal according to the acquired image of the object and output the image pickup signal to the processor 4.

The heating device 24 is configured to be driven (to generate heat), for example, while a heating device drive signal is supplied from the processor 4, and not to be driven (not to generate heat) while a heating device drive signal is not supplied from the processor 4. In other words, the heating device 24 is configured to generate heat for preventing fogging of the objective optical system 22 caused due to droplets, or the like (adhering to the objective optical system 22) according to supply of the heating device drive signal from the processor 4.

The temperature sensor unit 25 is configured to always detect a temperature of the distal end portion 2A when the endoscope 2 is activated, and to always output the detected temperature to the processor 4 as a temperature signal.

The light source device 3 has a light source such as a lamp and an LED and is configured to be able to supply an illumination light of a light amount according to a light adjustment signal outputted from the processor 4.

The processor 4 has a preprocessing unit 41, an A/D converting unit 42, an image processing unit 43, a D/A converting unit 44, a light adjusting unit 45, an image pickup device driving unit 46 and a control unit 47.

The preprocessing unit 41 is configured to perform processing such as signal amplification and noise removal on the image pickup signal outputted from the endoscope 2 and output the image pickup signal subjected to the processing to the A/D converting unit 42 and the light adjusting unit 45.

The A/D converting unit 42 is configured to convert the analog image pickup signal outputted from the preprocessing unit 41 into digital image data and output the digital image data to the image processing unit 43.

The image processing unit 43 is configured to perform processing such as gamma correction and edge enhancement on the image data outputted from the A/D converting unit 42 and output the image data subjected to the processing to the D/A converting unit 44.

The D/A converting unit 44 is configured to convert the image data outputted from the image processing unit 43 into an analog video signal and output the video signal to the display device 5.

The light adjusting unit 45 is configured to generate and output a light adjustment signal for adjusting a light amount of an illumination light supplied from the light source device 3 so that the brightness of the image pickup signal comes close to a predetermined brightness target value based on the image pickup signal outputted from the preprocessing unit 41.

The image pickup device driving unit 46 is configured to generate an image pickup device drive signal for causing acquisition of an image and generation (outputting) of an image pickup signal to be performed at a predetermined timing and output the image pickup device drive signal to the image pickup device 23.

The control unit 47 includes, for example, a CPU which is not illustrated, and is configured to be able to perform various control such as control for synchronizing operation of the image processing unit 43, the light adjusting unit 45 and the image pickup device driving unit 46. Further, the control unit 47 is configured to have a timer 47a capable of measuring a certain time period TP, which will be described later.

Further, the control unit 47 is configured to detect a temperature of the distal end portion 2A based on the temperature signal outputted from the temperature sensor unit 25 and supply a heating device drive signal to the heating device 24 (perform control to cause the heating device 24 to generate heat) when identification conditions (hereinafter, also simply referred to as predetermined conditions) are satisfied, the identification conditions being conditions for identifying whether or not the detected temperature of the distal end portion 2A is actually equal to or lower than a predetermined temperature, while not supplying a heating device drive signal to the heating device 24 (performing control not to cause the heating device 24 to generate heat) when the detected temperature of the distal end portion 2A does not satisfy the predetermined conditions.

More specifically, the control unit 47 estimates that the predetermined conditions are satisfied when detecting that a state where the temperature of the distal end portion 2A is equal to or lower than a temperature T1 continues for the certain time period TP (for example, 30 seconds) based on, for example, the temperature signal outputted from the temperature sensor unit 25 and the time period measured by the operation of the timer 47a, and starts supply of the heating device drive signal to the heating device 24. The control unit 47 supplies the heating device drive signal to the heating device 24 during a time period from when the control unit 47 detects that a state where the temperature of the distal end portion 2A is equal to or lower than the temperature T1 continues for the certain time period TP until when the control unit 47 detects that the temperature of the distal end portion 2A reaches a temperature T2 (>T1) based on the temperature signal outputted from the temperature sensor unit 25. On the other hand, the control unit 47 estimates that the predetermined conditions are not satisfied when detecting that a state where the temperature of the distal end portion 2A is equal to or lower than the temperature T1 does not continue for the certain time period TP based on, for example, the temperature signal outputted from the temperature sensor unit 25 and the time period measured by the operation of the timer 47a, and does not supply a heating device drive signal to the heating device 24.

Note that the above-described temperatures T1 and T2 are respectively set as temperatures (for example, T1=41° C. and T2=43° C.) according to the temperature within the body cavity of the subject which is a living body so as to be able to prevent fogging of the objective optical system 22 caused when observation is performed using the endoscope 2.

Further, the endoscope apparatus 1A according to the present embodiment is not limited to one in which the control unit 47 and the timer 47a are integrally provided, and may be one in which the control unit 47 and the timer 47a are separately provided.

Next, operation of the endoscope apparatus 1A according to the present embodiment will be described while referring to FIG. 2 as appropriate. FIG. 2 is a diagram for explaining an example of control performed in the endoscope apparatus according to the embodiment of the present invention.

The user powers on and activates each unit of the endoscope apparatus 1A and inserts the insertion portion of the endoscope 2 into the body cavity of the subject.

In the meantime, the control unit 47 starts detection of the temperature of the distal end portion 2A based on the temperature signal outputted from the temperature sensor unit 25 in association with activation of the processor 4.

When the control unit 47 detects that the temperature of the distal end portion 2A is equal to or lower than the temperature T1 based on the temperature signal outputted from the temperature sensor unit 25, the control unit 47 starts measurement of a time period using the timer 47a at time ta (see FIG. 2) corresponding to the timing at which detection is performed.

When the control unit 47 detects that the temperature of the distal end portion 2A exceeds the temperature T1 again at time tb (see FIG. 2) corresponding to an arbitrary timing before the certain time period TP has elapsed from the time ta based on the temperature signal outputted from the temperature sensor unit 25 and the time period measured by operation of the timer 47a, the control unit 47 stops measurement of the time period by the timer 47a and resets the time period measured by the timer 47a to 0.

That is, according to the control by the control unit 47 as described above, when a state where the temperature of the distal end portion 2A is equal to or lower than the temperature T1 does not continue for the certain time period TP, a heating device drive signal is not supplied to the heating device 24.

When the control unit 47 detects that the temperature of the distal end portion 2A is equal to or lower than the temperature T1 based on the temperature signal outputted from the temperature sensor unit 25, the control unit 47 starts measurement of a time period using the timer 47a at time tc (see FIG. 2) corresponding to the timing at which detection is performed.

When the control unit 47 detects that the temperature of the distal end portion 2A is still equal to or lower than the temperature T1 at time td (see FIG. 2) corresponding to a timing at which the certain time period TP has elapsed from time tc based on the temperature signal outputted from the temperature sensor unit 25 and the time period measured by the operation of the timer 47a, the control unit 47 stops measurement of a time period using the timer 47a and resets the time period measured using the timer 47a to 0 and starts supply of a heating device drive signal to the heating device 24.

Further, when the control unit 47 detects that the temperature of the distal end portion 2A reaches the temperature T2 based on the temperature signal outputted from the temperature sensor unit 25 after starting supply of a heating device drive signal to the heating device 24 (at time td), the control unit 47 stops supply of a heating device drive signal to the heating device 24 at time tc (see FIG. 2) corresponding to the timing at which detection is performed.

That is, according to the control by the control unit 47 as described above, when a state where the temperature of the distal end portion 2A is equal to or lower than the temperature T1 continues for the certain time period TP, a heating device drive signal is supplied to the heating device 24 until the temperature of the distal end portion 2A reaches the temperature T2.

As described above, according to the endoscope apparatus 1A according to the present embodiment, when a state where the temperature of the distal end portion 2A is equal to or lower than the temperature T1 does not continue for the certain time period TP, because it is identified that an erroneous temperature detection result is obtained based on a noise component mixed into the temperature signal outputted from the temperature sensor unit 25, a heating device drive signal is not supplied to the heating device 24 (the heating device 24 is not driven). Further, as described above, according to the endoscope apparatus 1A according to the present embodiment, when a state where the temperature of the distal end portion 2A is equal to or lower than the temperature T1 continues for the certain time period TP, because it is identified that a correct temperature detection result is obtained, a heating device drive signal is supplied to the heating device 24 (the heating device 24 is driven). As a result, according to the endoscope apparatus 1A according to the present embodiment, even when a correct temperature detection result cannot be obtained due to a noise component being mixed into the temperature signal outputted from the temperature sensor unit 25, it is possible to prevent erroneous operation of the defogging function which operates according to the temperature of the distal end portion 2A.

Note that according to the endoscope apparatus 1A of the present embodiment, for example, as illustrated in FIG. 1, it is also possible to configure an endoscope apparatus so that an amplifier 25A having a function as a signal amplifying unit is connected to an output terminal of the temperature sensor unit 25 at the distal end portion 2A, and a temperature signal amplified by the amplifier 25A is outputted to the processor 4. Further, according to this configuration, it is possible to prevent erroneous operation of the function which operates according to the temperature of the distal end portion 2A more reliably.

Figure 3:
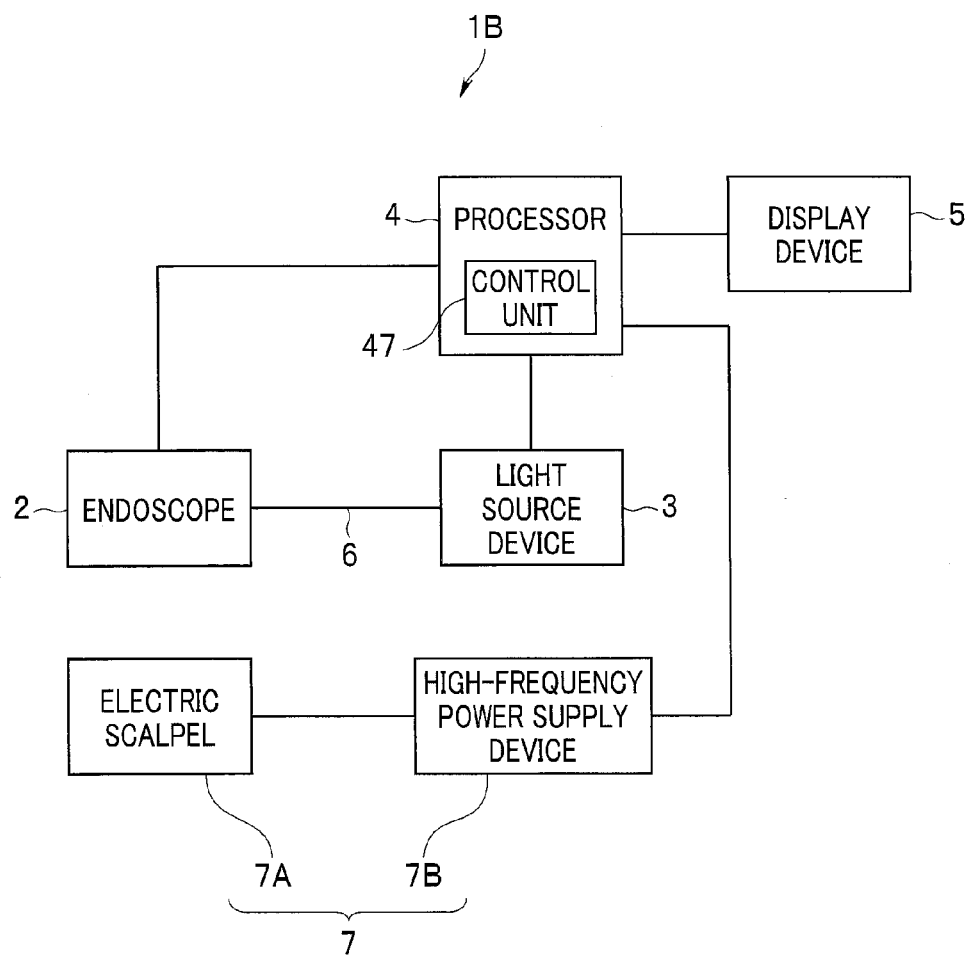
FIG. 3 is a diagram illustrating a configuration of main components of an endoscope apparatus according to a modification of the present invention.

On the other hand, when an endoscope apparatus 1B illustrated in FIG. 3 is used instead of the endoscope apparatus 1A illustrated in FIG. 1, control which will be described later may be performed by the control unit 47. FIG. 3 illustrates a configuration of the main components of the endoscope apparatus according to a modification of the present invention.

As illustrated in FIG. 3, the endoscope apparatus 1B is configured to have an endoscope 2, a light source device 3, a processor 4, a display device 5, a light guide 6 and an electric surgical apparatus 7 which can apply electrical energy to a portion to be treated within the body cavity of the subject.

The electric surgical apparatus 7 can be inserted into the body cavity of the subject and is configured to have an electric scalpel 7A which is configured to apply electrical energy to a portion to be treated located within the body cavity while a predetermined switch which is not illustrated is turned on, and a high-frequency power supply device 7B which has a function as a supply source of electrical energy to be applied by the electric scalpel 7A.

On the other hand, in the endoscope apparatus 1B having the above-described configuration, the control unit 47 detects whether or not the predetermined switch which is not illustrated is turned on (through the high-frequency power supply device 7B) and performs control so as to implement or stop supply of the heating device drive signal to the heating device 24 based on the detected result.

More specifically, when the control unit 47 of the endoscope apparatus 1B detects that the predetermined switch which is not illustrated is turned on, that is, when the electrical energy is applied to the portion to be treated from the electric scalpel 7A, even if the temperature of the distal end portion 2A detected based on the temperature signal outputted from the temperature sensor unit 25 is equal to or lower than the temperature T1, the control unit 47 of the endoscope apparatus 1B does not supply the heating device drive signal to the heating device 24.

In other words, when the control unit 47 of the endoscope apparatus 1B detects at least one of a case where the temperature of the distal end portion 2A detected based on the temperature signal outputted from the temperature sensor unit 25 exceeds the temperature T1 and a case where the electric scalpel 7A is running, the control unit 47 of the endoscope apparatus 1B estimates that the predetermined conditions are not satisfied and does not supply the heating device drive signal to the heating device 24.

Further, when the control unit 47 of the endoscope apparatus 1B detects that the predetermined switch which is not illustrated is not turned on, that is, when electrical energy is not applied to the portion to be treated from the electric scalpel 7A, the control unit 47 of the endoscope apparatus 1B starts supply of a heating device drive signal to the heating device 24 at a timing at which the temperature of the distal end portion 2A detected based on the temperature signal outputted from the temperature sensor unit 25 becomes equal to or lower than the temperature T1. Then, the control unit 47 of the endoscope apparatus 1B supplies the heating device drive signal to the heating device 24 until the temperature of the distal end portion 2A reaches the temperature T2 based on the temperature signal outputted from the temperature sensor unit 25.

In other words, when the control unit 47 of the endoscope apparatus 1B detects that the temperature of the distal end portion 2A detected based on the temperature signal outputted from the temperature sensor unit 25 is equal to or lower than the temperature T1 and that the electric scalpel 7A is not running, the control unit 47 of the endoscope apparatus 1B estimates that the predetermined conditions are satisfied and supplies the heating device drive signal to the heating device 24.

As described above, according to the endoscope apparatus 1B according to this modification, when a noise component generated according to operation of the electric scalpel 7A (application of the electrical energy to the portion to be treated) is mixed into the temperature signal outputted from the temperature sensor unit 25 and it is identified that an erroneous temperature based on the noise component is detected, a heating device drive signal is not supplied to the heating device 24 (the heating device 24 is not driven) regardless of whether or not the temperature of the distal end portion 2A is equal to or lower than the temperature T1. Further, as described above, according to the endoscope apparatus 1B according to this modification, when a noise component generated according to the operation of the electric scalpel 7A is not mixed into the temperature signal outputted from the temperature sensor unit 25 and it is identified that a correct temperature is detected, when the temperature of the distal end portion 2A is equal to or lower than the temperature T1, a heating device drive signal is supplied to the heating device 24 (the heating device 24 is driven). As a result, according to the endoscope apparatus 1B according to this modification, it is possible to prevent erroneous operation of the defogging function which operates according to the temperature of the distal end portion 2A.

Note that the endoscope apparatus 1B according to this modification is not limited to one which continuously applies electrical energy to the portion to be treated from the electric scalpel 7A while the predetermined switch which is not illustrated is turned on, but may be one which intermittently applies electrical energy to the portion to be treated from the electric scalpel 7A. More specifically, for example, it is also possible to apply electrical energy to the portion to be treated from the electric scalpel 7A only during a time period corresponding to a horizontal blanking period and a vertical blanking period of the image pickup signal outputted from the image pickup device 23 by performing control to synchronize operation of the image pickup device driving unit 46 and the high-frequency power supply device 7B. According to this configuration, for example, it is possible to reduce noise generated within an image to be displayed at the display device 5 when the endoscope 2 and the electric scalpel 7A are used at the same time.

The present invention is not limited to the above-described embodiment and modification, and naturally various alterations and applications are possible without departing from the spirit of the present invention.

What is claimed is:

1. An endoscope apparatus comprising:
    an objective optical system that is provided at a distal end portion of an insertion portion of an endoscope which can be inserted into a body cavity of a subject;
    a temperature sensor unit that detects a temperature of the distal end portion;
    a heating unit that can generate heat for preventing fogging of the objective optical system;
    a timer that measures a time period during which the temperature of the distal end portion detected by the temperature sensor unit is equal to or lower than a predetermined temperature; and
    a control unit that performs control so as to cause the heating unit to generate the heat when the time period measured by the timer continues for a predetermined time period or longer.

2. An endoscope apparatus comprising:
    an objective optical system that is provided at a distal end portion of an insertion portion of an endoscope which can be inserted into a body cavity of a subject;
    a temperature sensor unit that detects a temperature of the distal end portion;
    a heating unit that can generate heat for preventing fogging of the objective optical system;
    an electric surgical apparatus that applies electrical energy to a portion to be treated located within the body cavity; and
    a control unit that performs control so as to cause the heating unit to generate the heat when detecting that the temperature detected by the temperature sensor unit is equal to or lower than a predetermined temperature and that the electric surgical apparatus is not running.

* * * * *